United States Patent [19]
Gordon et al.

[11] 3,961,894
[45] June 8, 1976

[54] TEST FOR DETERMINATION OF TRIIODOTHYRONINE

[75] Inventors: Amirav Gordon; Jack Gross, both of Jerusalem, Israel

[73] Assignee: Yissum Research Development Company, Jerusalem, Israel

[22] Filed: Apr. 22, 1974

[21] Appl. No.: 462,882

[30] Foreign Application Priority Data
Apr. 24, 1973 Israel.................................. 42105

[52] U.S. Cl.............................. 23/230.6; 424/1.5; 250/303
[51] Int. Cl.²..................... G01N 33/16; G21H 5/02
[58] Field of Search............ 23/230 B, 230.6; 424/1, 424/12, 1.5; 250/303, 304

[56] References Cited
UNITED STATES PATENTS

| | | | |
|---|---|---|---|
| 3,659,104 | 4/1972 | Gross et al. .................... | 23/230 B X |
| 3,710,117 | 1/1973 | Gross et al. .................... | 23/230 B X |
| 3,711,247 | 1/1973 | Adams .............................. | 23/230 B |

OTHER PUBLICATIONS

Surks et al., *J. Clin. Invest.*, vol. 51, pp. 3104–3113 (1972).

Alexander et al., *Clin. Chem.*, vol. 20, pp. 1353–1361 (1974).

*Primary Examiner*—Morris O. Wolk
*Assistant Examiner*—Timothy W. Hagan
*Attorney, Agent, or Firm*—Andrew L. Klawitter

[57] ABSTRACT

A radioimmunoassay method for the determination of triiodothyronine in human and animal fluids and tissues, particularly in serum. The method involves the separation of triiodothyronine from its binding proteins using a dextran gel column followed by competitive binding between the freed triiodothyronine and radioactive labeled triiodothyronine which remain bound to the gel column for triiodothyronine-specific anti-serum. Bound and free labeled triiodothyronine are separated by washing the column and their ratio is determined based on the amount of radioactivity remaining in the column to that originally added thereto.

11 Claims, 1 Drawing Figure

U.S. Patent June 8, 1976 3,961,894
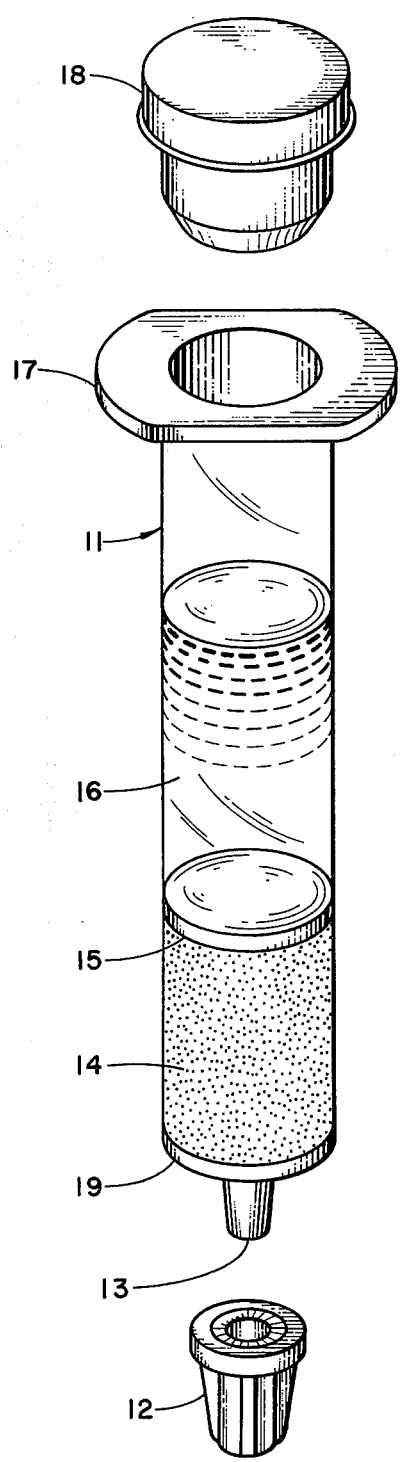

TEST FOR DETERMINATION OF TRIIODOTHYRONINE

The present invention relates to a novel method and device for the determination of triiodothyronine, designated hereinafter as $T_3$. More particularly, the present invention relates to a novel quantitative specific radioimmunoassay for the determination of $T_3$ in human and animal fluids and tissues, and especially in human sera. Other and further features of the present invention will become apparent hereinafter.

Triiodothyronine or $T_3$ is now considered to be the active form of thyroid hormone, and therefore, measurements of the quantity of $T_3$ in the serum reflects the thyroidal status more closely than other thyroid function determinations. Furthermore, conditions have been described in which the only thyroid hormone abnormality was an increase in the level of $T_3$, a condition described as $T_3$ Thyrotoxicosis.

There are known various methods for the quantitative determination of $T_3$ in biological materials, but these are quite timeconsuming and complicated. According to the present invention there is provided a simple, comparatively rapid and reproducible radioimmunoassay for the specific determination of $T_3$. The interference of $T_4$ (thyroxine) is so small as to be practically negligible.

The novel method of the present invention may be carried out using a test device which comprises essentially a cylindrical tubular body 11 having a fixed geometry and terminating at one end in a tapered tip portion 13. The body 11 is formed of polypropylene or other suitable material and is provided with valve means, such as a friction fit cap 12, which fits over and removably closes the tip portion 13. A quantity of cross linked dextran gel 14, which will be more completely described hereinafter, is retained between two porous polyethylene discs 15 and 19 in the lower portion of the body 11. A buffer or the reaction mixture 16 may be retained in the upper portion of the body 11 as shown. The upper end of the body 11 may be formed with an outwardly projecting flange 17 for ease of holding the body 11 in an upright position in a suitable rack and a removable cap 18 is provided for sealing the upper end of the body 11 and thereby preventing the column from drying out during storage or shipment.

As noted above, the basic chemical constituent of the test device of the present invention is the column 14 of cross linked dextran gel retained in the lower end of the body 11. A preferred dextran gel is that known commercially as Sephadex. This material is a cross linked polysaccharide having the ability to act as a molecular sieve, i.e. it retains molecules in various degrees depending upon their size and to some extent their charge. The use of this dextran gel technique as a molecular sieve is often called gel filtration. Sephadex G-25, a type of dextran gel which excludes materials of greater than 2000 to 3000 molecular weight from the grains, is insoluble in water and salt solutions and is very stable in alkalies and weak acids. Such a substance is preferable for use in the present invention. Sephadex G-15 and G-10 can also be adapted to serve the same purpose.

The test device of the present invention may advantageously be prepared by initially hydrating the dry dextran gel with an appropriate buffer (as will be described hereinafter). About 450 mg. (on a dry basis) of gel 14 is placed on the lower one third of the body 11 between porous polyethylene discs 15 and 19. The body 11 illustrated has an inside diameter of about 13 mm. and a total length of about 7.6 cm., and the discs 15 and 19 have a diameter of 13 mm. The gel 14 occupies a volume of about 2.5 ml. While the above materials and sizes are merely exemplary, it has been found that such a geometry ideally fits the counting well of certain commercial radiation counting instruments, such as the Gammacord gamma counter.

As far as the method of the present invention is concerned, it has been found that the previously described test device, coupled with the utilization of a small quantity of sample, such as serum, results in a thyroid function test device and method which has several unexpected and important advantages. By a small quantity of serum sample, it is meant a sample size which may range from about 0.1 ml. to about 0.5 ml. By using a small serum sample in combination with an amount of radioactive tagged thyroid hormone appropriate for the test system being utilized, a test is effected which has all the advantages previously mentioned, i.e. a single reaction device and counting vessel, universal application and so forth.

The method according to the present invention, which is specific for the quantitative determination of $T_3$, is a modification of an isotope dilution technique.

According to the present invention, the method comprises:

a. Admixing at the top of the column a predetermined quantity of serum or other biological fluid and a predetermined quantity of radioactive labeled $T_3$ made up in a solution having either pH higher than 10.5 or lower than pH 3.

b. Equilibrating the mixture for a predetermined period of time;

c. Introducing the equilibrated mixture into the column of dextran gel prepared in a suitable solution having a pH less than 3 or more than 10.5;

d. Washing out substantially all the proteins by means of a liquid (preferably a buffer) of a pH between 6 – 9;

e. Introducing into the column a predetermined quantity of $T_3$- specific anti-serum, adapted to bind part of the total $T_3$ content of the column;

f. Making a count of the radioactivity of the column;

g. Incubating the anti-serum and the $T_3$ in the column for a predetermined period of time;

h. Washing out the anti-serum-bound $T_3$ by means of a suitable buffer;

i. Making a further count of the radioactivity of the column;

j. Determining the $T_3$ content of the sample from a previously prepared calibration curve.

The calibration curve is prepared as set out in the above procedure, with the only difference that known samples of $T_3$ and $T_3^{125}$I are mixed and a calibration curve is prepared.

A small quantity of serum is sufficient for the quantitative determination according to the present invention. An example of such determination is described henceforth:

0.3 ml. of serum is admixed at the top of the column with 0.7 ml. of $T_3^{125}$I in 0.1 N NaOH and left for a period of about 15 minutes in order to attain an equilibrium between the protein bound $T_3$ and the added radioactive $T_3$. After this period of time the mixture is introduced by gravity flow into the dextran gel of the column which was prepared in 0.1 N NaOH. The triiodothyronine is adsorbed on the gel and after this the serum protein is eluted in a substantially quantitative manner with 4 ml. of 0.1 N phosphate buffer of pH 7.4. While the protein is eluted, over 98% of the $T_3$ and $T_3{}^{125}$ I remains on the column.

A quantity of 0.5 ml. of dilute $T_3$-anti-serum is pipetted onto the column and allowed to drain into the incubate within the column for 2 hours. The quantity of anti-serum is chosen so as to bind a part of the $T_3$ only. During the 2 hour incubation period, the first count of radioactivity is taken. At the end of this period the anti-serum-bound $T_3$ is washed out by means of 4 ml. of the same buffer and the second count of the radioactivity is taken. The quantity of $T_3$ in the serum is read off from the calibration curve, which is prepared beforehand. This calibration curve is prepared by means of a substantially identical procedure; only instead of the unknown serum there is taken a standard solution of $T_3$. The entire test takes only about 3 hours. The standard curve is rather constant, the variance of the slope of 6 separate curves being 6.6%. By such means the value of $T_3$ in a Euthyroid sera was found to be 168 mg./ 100cc. whereas sera from hypothyroid patients gave distinctly lower values and sera from hyperthyroid patients gave distinctly higher values.

The anti-sera in this example were prepared in rabbits against a conjugate of bovine serum albumin and purified $T_3$ according to the following procedure:

1. $T_3$ was cleaned by purification in 2N HCl according to the method of Gross T. and P.H. Rivers R; *Biochemical Journal* 53, 645 (1953).
2. $T_3$ was conjugated to bovine serum albumin and antiserum against this conjugate was prepared according to the method described by Gharib H., et al.; *J. Clin Endocr.* 31, 709 (1970). However, $T_3$ may be conjugated to other carrier polymer such as Human Serum albumin, hemocyanin (Keyhole Limpet), poly L-Lysine, or others. These conjugates are equally effective in eliciting proper anti-$T_3$ anti-serum in suitable animals.
3. The titer of anti-serum used in the test was determined as the dilution of anti-serum sufficient to remove 30% of the hormone ($T_3$) when tested against a standard serum containing 5 ng/ml. $T_3$.

The following results were obtained:

As $T_4$ is present in serum in a much larger quantity than $T_3$, it was important to determine whether and to what extent the presence of $T_4$ interferes with the determination of $T_3$. A standard serum was loaded with $T_4$ to levels exceeding 40 mg% and $T_3$ was determined as a function of the increase of the content of $T_4$. The level of interference was 0.11% and this can be neglected.

We claim:

1. A method for the in vitro determination of triiodothyronine in a biological fluid sample comprising the steps of:
    a. adding to a column containing a crosslinked dextran gel at a pH of at least about 10.5 or less than about 3 a predetermined quantity of said fluid sample and a quantity of radioactive labeled triiodothyronine,
    b. washing said column with an aqueous solution having a pH of between about 6 and 9,
    c. adding to said column a predetermined quantity of antibody to triiodothyronine,
    d. incubating said column,
    e. washing said column with an aqueous solution to substantially remove the antibody-bound-triiodothyronine,
    f. determining the ratio of radioactive labeled triiodothyronine retained in said column after step (e) to that added in step (a), and
    g. comparing the ratio determined in step (f) to ratios obtained using standard samples containing known amounts of triiodothyronine.

2. A method as in claim 1 wherein said predetermined quantity of said fluid sample and said quantity of radioactive labeled triiodothyronine added to said column in step (a) are first combined and equilibrated before introduction into said column of dextran gel.

3. A method as in claim 2 wherein said predetermined quantity of antibody of triiodothyronine added to said column in step (c) is in the form of anti-serum prepared in a suitable laboratory animal against a conjugate of triiodothyronine and a suitable carrier.

4. A method as in claim 2 wherein said dextran gel is cross-linked with epichlorohydrin and has a water regain of from about 1 to 5 grams per gram of dry gel.

5. A method as in claim 4 wherein the amount of radioactivity contained in said column is measured

| Status | $T_3$ range in mg% |
|---|---|
| Hypothyroid (12 patients) | 66 – 110 |
| Euthyroid (19 patients) | 130 – 281 |
| Hyperthyroid (23 patients) | 291 – 2047 |

Reproducibility Determined by the Calibration Curves Parameters and $T_3$ Values of a Control Serum
Calibration Curve
(*B/F vs. Ln $T_3$ concentration)

| Exp. | Slope | Intercept | Coefficient Correlation | $T_3$ mg% in control serum |
|---|---|---|---|---|
| 104 | −3.77 | 9.39 | 0.988 | 167 |
| 104A | −3.36 | 9.10 | 0.986 | 159 |
| 105 | −3.33 | 9.03 | 0.986 | 204 |
| 110 | −3.21 | 8.93 | 0.986 | 153 |
| 111 | −3.12 | 8.78 | 0.984 | 168 |
| 112 | −3.28 | 8.85 | 0.996 | 160 |
| Mean ± SD | −3.34±.22 | 9.01±.21 0.988±.004 | | 168±18 |

$$*B/F = \frac{\text{Bound } (T_3)}{\text{Free } (T_3)}$$

once after step (*c*) but before step (*e*) and again after step (*e*).

6. A method as in claim 1 wherein said column in step (*a*) is at a pH of at least 10.5.

7. A method as in claim 1 wherein the quantity of radioactive labeled triiodothyronine added to said column in step (*a*) is predetermined and the amount of radioactivity contained in said column is measured after step (*e*).

8. A method as in claim 1 wherein the radioactivity contained in said column is measured before and after step (*e*).

9. A method as in claim 1 wherein said aqueous solution used in step (*e*) has a pH of between about 6 and 9.

10. A method as in claim 9 wherein said aqueous solution contains a phosphate buffer.

11. A method as in claim 1 wherein said biological fluid sample is serum.

* * * * *